(12) United States Patent
Binkley et al.

(10) Patent No.: US 12,320,730 B2
(45) Date of Patent: Jun. 3, 2025

(54) EXTENDABLE POOL WATER COLLECTION AND TESTING DEVICE

(71) Applicants: Thomas Binkley, Oakland, FL (US); Kim Binkley, Oakland, FL (US)

(72) Inventors: Thomas Binkley, Oakland, FL (US); Kim Binkley, Oakland, FL (US)

(*) Notice: Subject to any disclaimer, the term of this patent is extended or adjusted under 35 U.S.C. 154(b) by 0 days.

(21) Appl. No.: 18/635,501

(22) Filed: Apr. 15, 2024

(65) Prior Publication Data

US 2024/0385084 A1    Nov. 21, 2024

Related U.S. Application Data

(60) Provisional application No. 63/472,988, filed on Jun. 14, 2023, provisional application No. 63/466,945, filed on May 16, 2023.

(51) Int. Cl.
*G01N 1/12* (2006.01)
*G01N 33/18* (2006.01)

(52) U.S. Cl.
CPC ........... *G01N 1/12* (2013.01); *G01N 33/1886* (2013.01)

(58) Field of Classification Search
CPC ...... G01N 1/12; G01N 33/1886; G01N 33/18; G01N 2291/2695; C02F 2103/42
See application file for complete search history.

(56) References Cited

U.S. PATENT DOCUMENTS

| | | | | |
|---|---|---|---|---|
| 2,802,230 A | * | 8/1957 | Maddox | A47L 13/24 15/229.8 |
| 3,692,490 A | * | 9/1972 | Hall | G01N 1/12 4/488 |
| 4,180,009 A | * | 12/1979 | Voss | G01N 33/182 356/246 |
| 2006/0179961 A1 | * | 8/2006 | Schaub | G01N 1/12 73/864.63 |

* cited by examiner

*Primary Examiner* — Tarun Sinha
(74) *Attorney, Agent, or Firm* — Jason T. Daniel, Esq.; Daniel Law Offices, P.A.

(57) ABSTRACT

An extendable pool water testing and collection device includes a pair of test chambers along a front end, and a basin for receiving and collecting large samples of water. The front wall of the main body is transparent for viewing water within the chambers and includes a plurality of reagent color indicator markings. A funnel is provided along one side of the main body for dispensing water from the basin into a secondary object. A pair of removable caps are provided for the chambers, and a single lid covers each of the basin and the chambers. An extendable handle having an articulating joint is connected to the top end of the main body for allowing a user to submerge the chambers and basin into a body of water without kneeling or bending.

16 Claims, 6 Drawing Sheets

EXTENDABLE POOL WATER COLLECTION AND TESTING DEVICE

CROSS-REFERENCE TO RELATED APPLICATIONS

This application claims the benefit of U.S. Application Ser. No. 63/466,945 filed on May 16, 2023, and U.S. Application Ser. No. 63/472,988 filed on Jun. 14, 2023, the contents of each of which are incorporated herein by reference.

TECHNICAL FIELD

The present invention relates generally to water testing kits, and more particularly to an extendable pool water collection and testing device.

BACKGROUND

The statements in this section merely provide background information related to the present disclosure and may not constitute prior art.

As any pool owner will attest, it is critically important to regularly test and adjust chemicals within pool water to maintain a clean and safe swimming area. In this regard, many users routinely utilize a portable test kit that can be dipped into the pool to capture a small sample of water within a chamber. Once captured, a reagent, indicator solution or test strip is added to the sample, in order to provide the user with basic water characteristics such as pH levels and chlorine, for example.

Aside from these kits, many users will often retrieve a second sample of water from the pool and bring the same to a local pool store in order to perform more comprehensive tests, such as Free and Total Chlorine, total Alkalinity, Calcium hardness, and cyanuric acid, among others, for example. In either instance, once the tests have been completed, the user can add additional chemicals to the pool water in order to bring the overall chemical composition in line with desired norms.

Unfortunately, many elderly individuals, or those who suffer from physical ailments such as back or neck problems have difficulty bending and dipping the test kit and the sample cup below the water surface in order to obtain a water sample. Indeed, each year there are reports of individuals who accidentally fall into their swimming pool while performing simple maintenance items such as this. Tragically, some of these incidents have resulted in injuries and death. For these reasons, some individuals forego obtaining water samples, thus resulting in their pools becoming overrun with unsafe bacteria and algae.

Accordingly, it would be beneficial to provide an extendable pool water testing and collection device that can allow users to easily and safely obtain multiple water samples from a body of water so as to alleviate the drawbacks noted above.

SUMMARY OF THE INVENTION

The present invention is directed to an extendable pool water testing and collection device. One embodiment of the present invention can include a main body having a pair of testing chambers along a front end, and a hollow middle section defining a basin for receiving and collecting large samples of water. In one embodiment, the front wall of the main body can be transparent for viewing water within the chambers and can include a plurality of markings. Each of the markings can include at least one color that corresponds to a color the stored water will turn upon receiving a reagent within the chamber.

In one embodiment, the basin can include a funnel along one side for accurately dispensing water from the basin into a secondary object. Each of the chambers can include removable caps for allowing a user to shake the device when performing a chemical test. The basin can include a removeable lid for storing the water within the basin for transport.

In one embodiment, a handle can be connected to the main body. The handle can be removably connected via a connector and can include an articulating joint for allowing a user to manipulate the orientation of the main body relative to the handle. The handle can also be telescopic in nature so as to allow a user to adjust a length of the handle and for permitting a user to dip the chambers and basin into a body of water without kneeling or bending. In another embodiment, test strip chambers and a storage compartment can also be provided along the main body.

This summary is provided merely to introduce certain concepts and not to identify key or essential features of the claimed subject matter.

BRIEF DESCRIPTION OF THE DRAWINGS

Presently preferred embodiments are shown in the drawings. It should be appreciated, however, that the invention is not limited to the precise arrangements and instrumentalities shown.

DETAILED DESCRIPTION OF THE INVENTION

Figure 1:
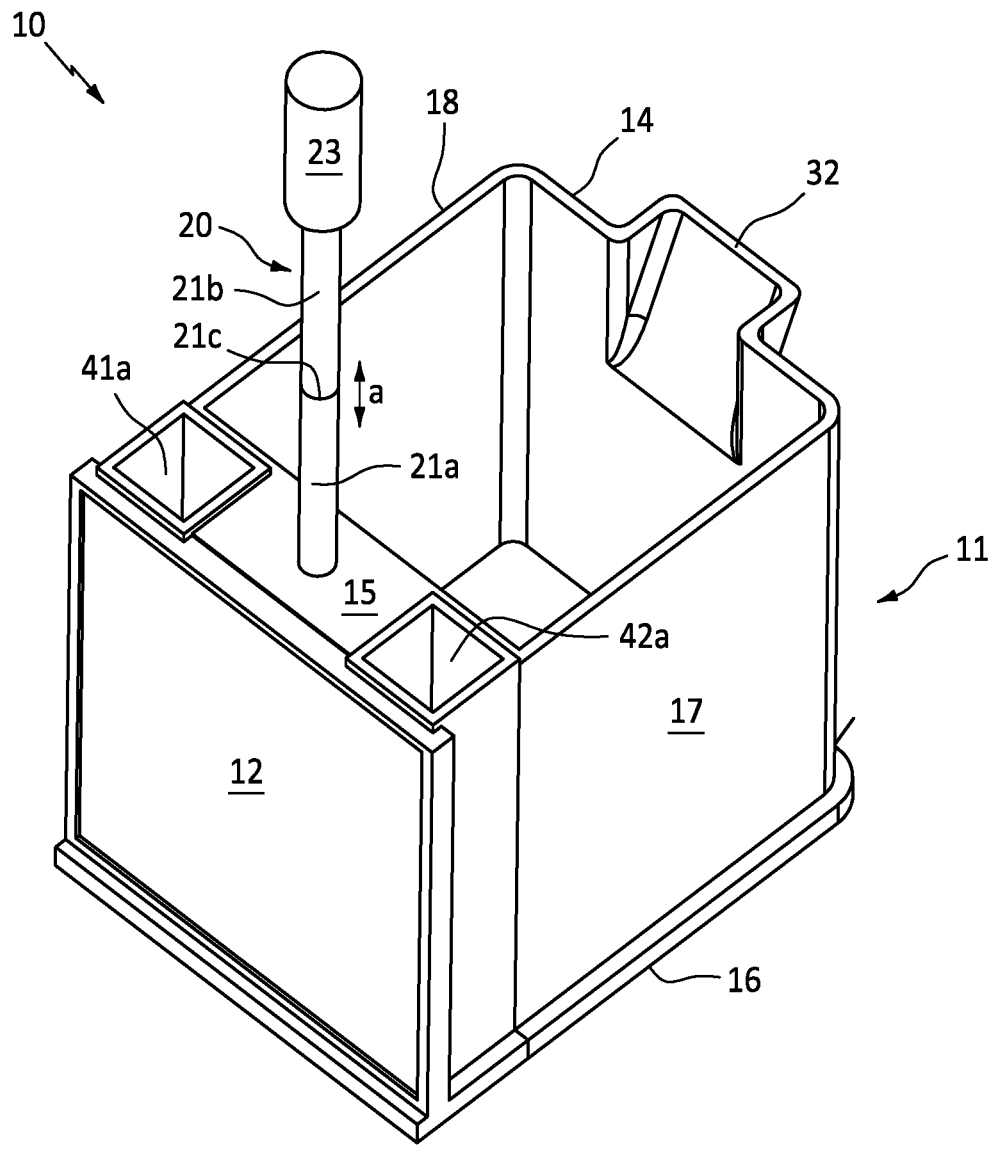
FIG. 1 is a perspective view of an extendable pool water collection and testing device that is useful for understanding the inventive concepts disclosed herein.

While the specification concludes with claims defining the features of the invention that are regarded as novel, it is believed that the invention will be better understood from a consideration of the description in conjunction with the drawings. As required, detailed embodiments of the present invention are disclosed herein; however, it is to be understood that the disclosed embodiments are merely exemplary of the invention which can be embodied in various forms. Therefore, specific structural and functional details disclosed herein are not to be interpreted as limiting, but merely as a basis for the claims and as a representative basis for teaching one skilled in the art to variously employ the inventive arrangements in virtually any appropriately detailed structure. Further, the terms and phrases used herein are not intended to be limiting but rather to provide an understandable description of the invention.

Definitions

As described herein, a "unit" means a series of identified physical components which are linked together and/or function together to perform a specified function.

As described throughout this document, the term "about" "approximately" "substantially" and "generally" shall be used interchangeably to describe a feature, shape, or measurement of a component within a tolerance such as, for example, manufacturing tolerances, measurement tolerances or the like.

As described herein, the term "removably secured," and derivatives thereof shall be used to describe a situation wherein two or more objects are joined together in a non-permanent manner so as to allow the same objects to be repeatedly joined and separated.

As described throughout this document, the term "complementary shape," and "complementary dimension," shall be used to describe a shape and size of a component that is identical to, or substantially identical to the shape and size of another identified component within a tolerance such as, for example, manufacturing tolerances, measurement tolerances or the like.

As described herein, the term "slidingly engage", "telescopically connected" and derivatives thereof shall be used interchangeably to describe a situation wherein two identified objects are connected linearly such that one identified part slides into and out from the other identified part so as to selectively lengthen or shorten the total linear length of both parts.

As described herein, the term "connector" includes any number of different elements that work alone or together to repeatedly join two items together in a nonpermanent manner. Several nonlimiting examples of connectors include, but are not limited to, flexible strips of interlocking projections with a slider (i.e., zipper), thread-to-connect, twist-to-connect, and push-to-connect type devices, opposing strips of hook and loop material (e.g., Velcro®), attractively oriented magnetic elements or magnetic and metallic elements, buckles, and compression fittings, for example. Each illustrated connector and complementary connector can be permanently secured to the illustrated portion of the device via a permanent sealer such as glue, adhesive tape, or stitching, for example.

FIGS. 1-6 illustrate one embodiment of an expandable pool water testing device 10 that are useful for understanding the inventive concepts disclosed herein. In each of the drawings, identical reference numerals are used for like elements of the invention or elements of like function. For the sake of clarity, only those reference numerals are shown in the individual figures which are necessary for the description of the respective figure. For purposes of this description, the terms "upper," "bottom," "right," "left," "front," "vertical," "horizontal," and derivatives thereof shall relate to the invention as oriented in FIG. 1.

Although described and illustrated with regard to collecting water from a pool, this is but one possible use of the inventive device. As such, the invention is not to be construed as limiting to the pool industry as any number of other uses and industries are contemplated.

As shown in the drawings, the device 10 can include, essentially, a main body 11 having a sample collection basin 30 and a pair of liquid reagent test chambers 41 and 42, which can be dipped into a body of water from a standing position via a handle 20.

As shown in the drawings, the main body 11 can include a front wall 12, an inside wall 13, a back wall 14, a top wall 15, a bottom wall 16, and a pair of side walls 17 and 18. As described herein, the main body may be formed from materials that are, for example, relatively strong and stiff for their weight while remaining suitable for prolonged exposure to fresh or salt water without corroding. Several non-limiting examples include but are not limited to various metals or metal alloys (e.g., aluminum, titanium, or alloys thereof), plastic/polymers (e.g., high-density polyethylene (HDPE), rigid polyvinyl chloride (PVC), and/or various composite materials (e.g., carbon fibers in a polymer matrix, fiberglass, etc.).

In one embodiment, the device can include an elongated handle 20 which can extend from the top wall 15 in order to allow a user to easily lower and dip the device into a body of water such as a swimming pool, for example, without having to bend or kneel. In the preferred embodiment, the handle can be telescopic in nature, so as to allow a user to adjust the length of the handle from about 6 inches to about 36 inches, for example. Of course, other lengths are also contemplated.

In this regard, the handle can include a fixed lower section 21a that is secured to the top wall 15, and at least one sliding upper section 21b that extends from and retracts into the fixed lower section 21a (see arrow a). A tensioning ring 21c can be provided along the end of the fixed section to secure the sliding section(s) at a user defined height.

Figure 2:
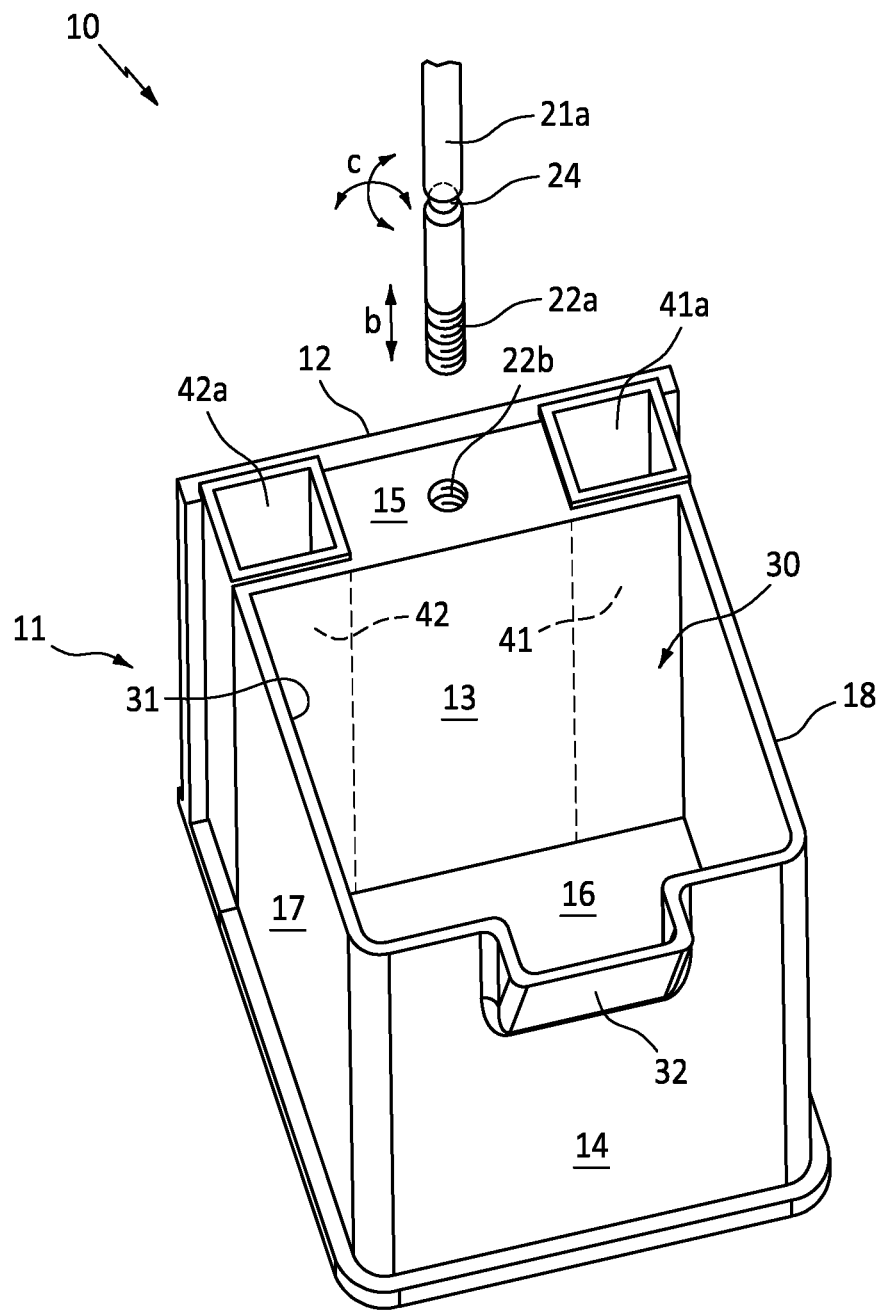
FIG. 2 is a top view of the extendable pool water collection and testing device in accordance with one embodiment of the invention.

As shown best at FIG. 2, one embodiment of the handle can include a plurality of threaded elements 22a that are configured to engage (see arrow b) a plurality of complementary threaded elements 22b extending downward from the top wall 15, in order to removably secure the handle to the main body in a twist-to-connect manner. Additionally, the present embodiment of the handle can include an articulating joint 24 to permit the handle to pivot or rotate in any number of different directions (see arrow c) relative to the main body. Such a feature allowing the user to orient the main body in any number of different directions for accessing water from a pool or other structure, as will be described below.

Of course, any number of other connectors capable of removably connecting the handle to the main body are also contemplated. Moreover, other embodiments are contemplated wherein the handle is not removeable from the main body and/or wherein the articulating joint is located elsewhere, or is not provided at all, thus resulting in a fixed handle.

In either instance, the top end of the handle can preferably include a hand grip 23 which may be constructed from any number of materials suitable for increasing the coefficient of friction between a user's hand and the handle and/or for increasing the comfort of a user gripping the handle. Several nonlimiting examples of hand grips for use herein include, but are not limited to, various foam or rubber formulations, for example. Of course, any number of other materials are also contemplated, and the hand grip may also include any number of different shapes and sizes such as a plurality of protrusions and indentations for individually accommodating the fingers of a user gripping the device.

In one embodiment, the device 10 can include a sample collection basin 30 that can function to easily capture water samples for external testing or any number of other purposes. As such, the basin can include an opening 31 that is formed along the top end of the main body. The opening can provide access to a hollow watertight interior space that is defined by the middle wall 13, the back wall 14, and side walls 17 and 18. In the preferred embodiment, the basin will be sized to receive and store about 6 ounces of water; however, other embodiments are contemplated wherein the basin can store different amounts of water.

In one embodiment, the basin can include a spout 32 that extends outward from the back wall 14. The spout can function to allow a user to easily and precisely pour water from the collection basin into a secondary device such as a bottle or piece of test equipment, for example. Although illustrated with regard to a generally rectangular-shaped collection basin and a centrally located spout, any number of other shapes are contemplated and the spout can be located at other locations such as along the front or sidewalls of the main body, for example.

Figure 3:
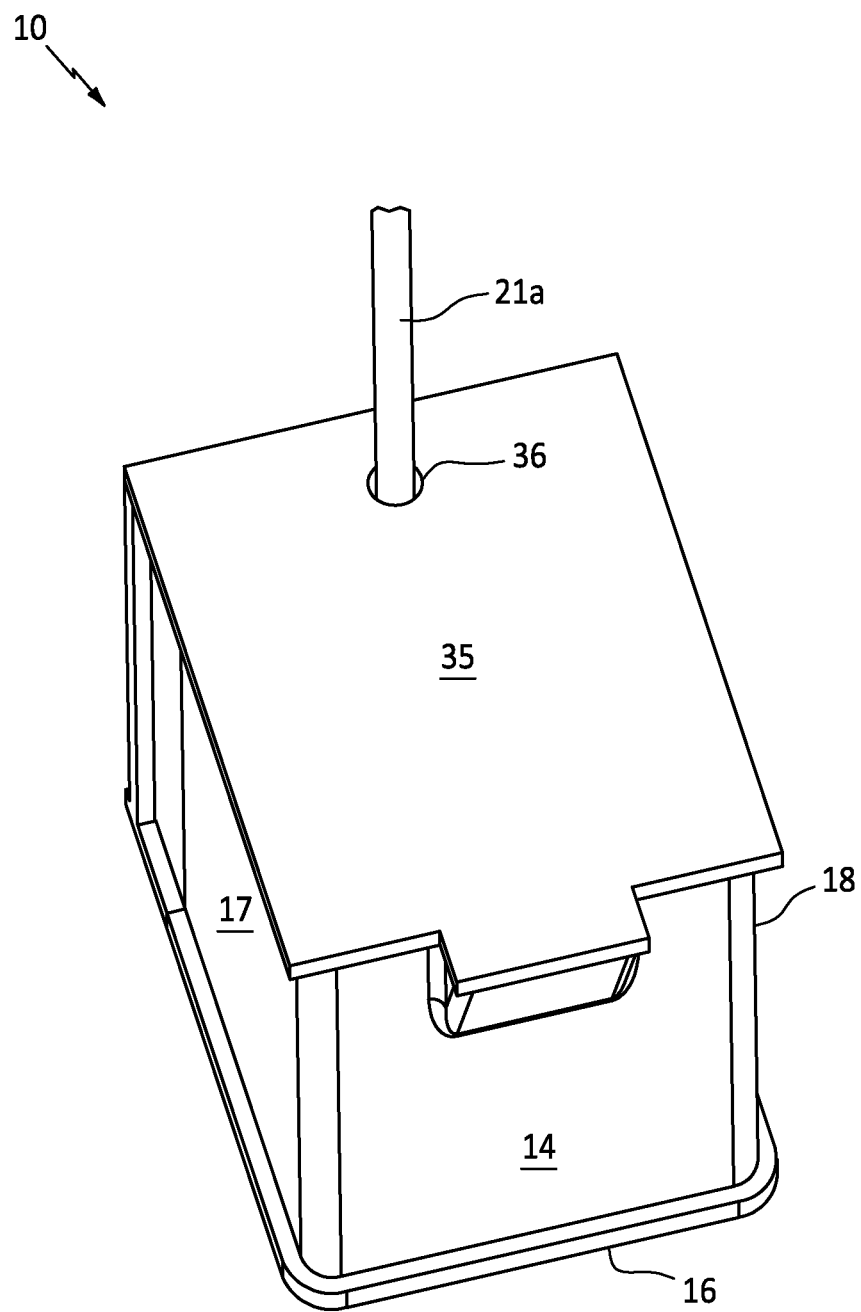
FIG. 3 is another top view of the extendable pool water collection and testing device in accordance with one embodiment of the invention.
Figure 4:
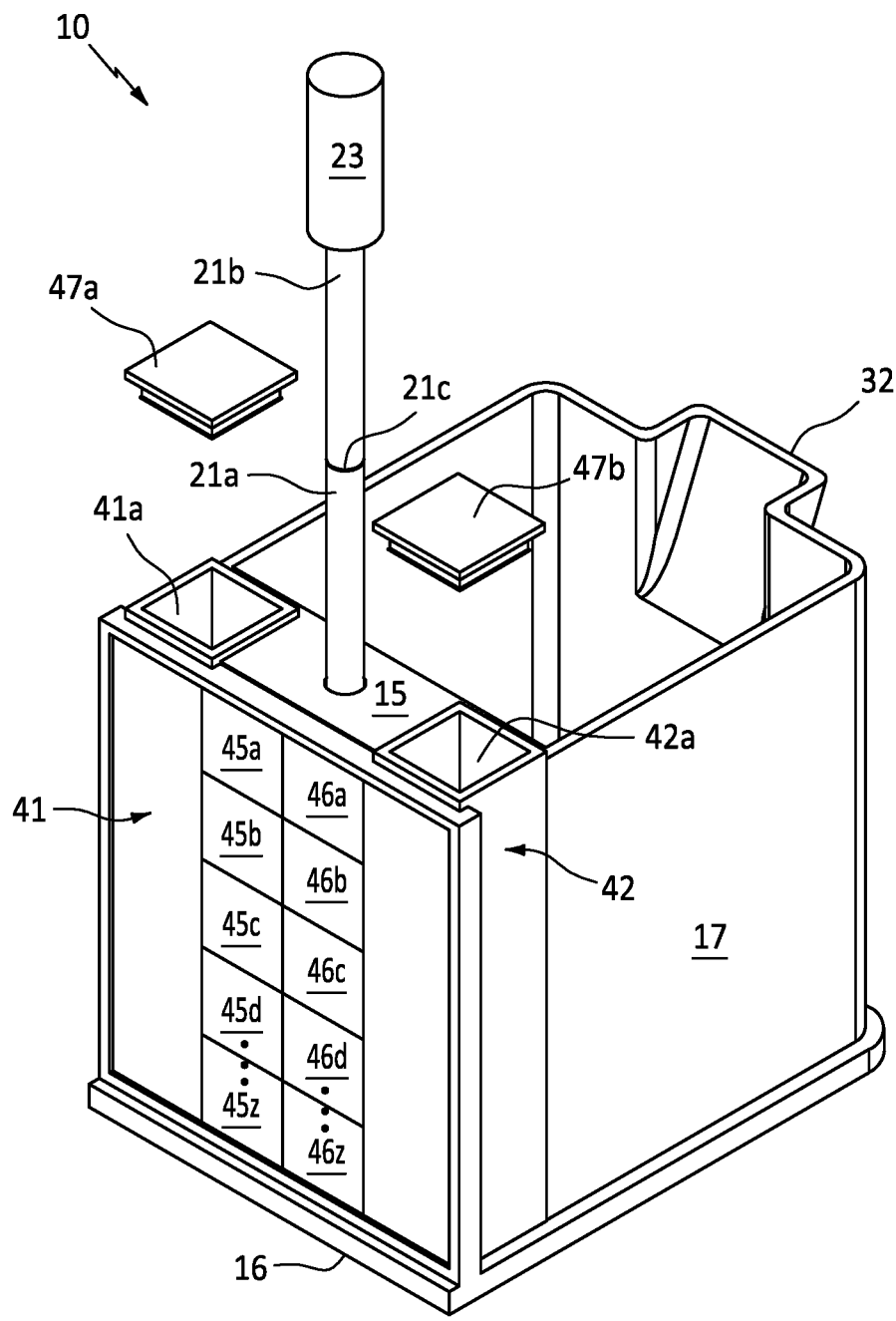
FIG. 4 a perspective view of the extendable pool water collection and testing device in accordance with one embodiment of the invention.

As shown at FIG. 3, the device 10 can also include a basin lid 35 which can function to seal both the below described test chambers 41 and 42, along with the opening 31 of the basin in a watertight manner for allowing the user to store and/or transport the device with water in the collection basin and/or the chambers. In this regard, the lid 35 can include a shape and size that is complementary to the top end of the main body and can be constructed from a malleable material such as rubber or flexible plastic, for example.

In operation, the lid can be positioned above and pressed over the top of the main body in order to cover the chambers 41 and 42, the opening 31 and spout 32, thereby ensuring water within the main body will not leak. In one embodiment, the lid can also include a hole 36 that is complementary in location and dimensions to the diameter of the handle 20, so as to allow the lid to be positioned over the device without having to remove the handle.

In one embodiment, the device 10 can include a pair of liquid reagent test chambers 41 and 42, which can ideally be located along the front end of the main body. Each of the test chambers can function to receive and store a measured amount of water for chemical or strip testing and can function to keep this water separate from the water sample located in the basin. As shown, the test chambers can include generally rectangular-shaped chambers that extend continuously downward from the top wall 15 to the bottom wall 16. Openings 41*a* and 42*a* are provided to permit the water to enter the chambers.

In one embodiment, the front wall 12 will be transparent in nature, so as to allow a user to easily see the water within each chamber 41 and 42. Likewise, the side walls 17 and 18 or portions thereof that define the sides of the chambers 41 and 42 can also be transparent. Additionally, a plurality of colored markings 45*a*-45*z* and 46*a*-46*z* can be provided along the front wall 12 adjacent to chambers 41 and 42, respectively. Each of the colored markers can correspond to a different color to which water inside the corresponding chamber will change upon receiving a reagent material such as DPD (NN Diethyl p Phenylene Diamine Sulphate), or Phenol Red, for example. Based on the resulting color, the user will know what chemicals to add to the pool or other body of water from which the samples were collected in order to bring the same into acceptable standards.

In one embodiment, a pair of test chamber caps 47*a* and 47*b* can be provided. As shown, the caps can include a truncated bottom end which can be inserted through the chamber openings 41*a* and 42*a*, respectively, to allow the caps to seal the collected water within the chambers. Such a feature allows the user to vigorously shake the device to mix the reagent with the collected water sample within the chambers when performing the above noted tests.

Although illustrated above with regard to two identical-shaped and sized chambers located along the front of the main body with colored markings for allowing a user to perform a chemical water test, other embodiments are contemplated. To this end, any number of other chambers may be provided, each having any number of different shapes and sizes, and can be located at other locations along or within the main body.

Figure 5:
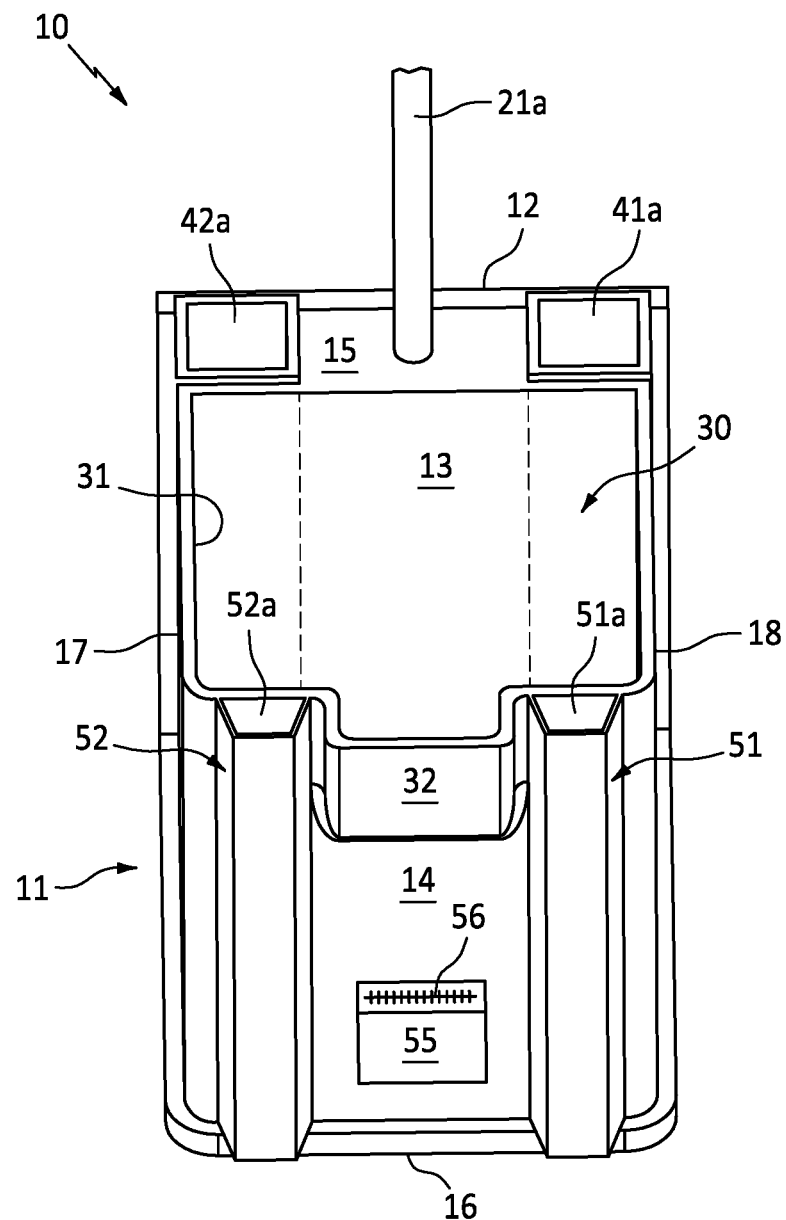
FIG. 5 is a back view of the extendable pool water collection and testing device in accordance with one embodiment of the invention.

As such, FIG. 5 illustrates one embodiment of the device 10 that includes a second set of chambers 51 and 52 which can be located along the back end of the main body. Chambers 51 and 52 can also include openings 51*a* and 52*a* for receiving water samples and test strips having a plurality of integrated markings which alter in appearance based on a reaction with water. In this regard, the chambers 51 and 52 will be constructed from a transparent material ideally having no markings whatsoever in order to permit a user to view the test strip within the water through the walls of the chamber.

Finally, one embodiment of the device 10 can include a watertight pocket 55 that is located along the outside surface of the main body. The pocket can provide a dry waterproof cavity having a resealable opening 56 such as a watertight zipper or other form of waterproof connector, for example, to allow the pocket to store unused chemical test strips and/or chemical reagents.

Figure 6:
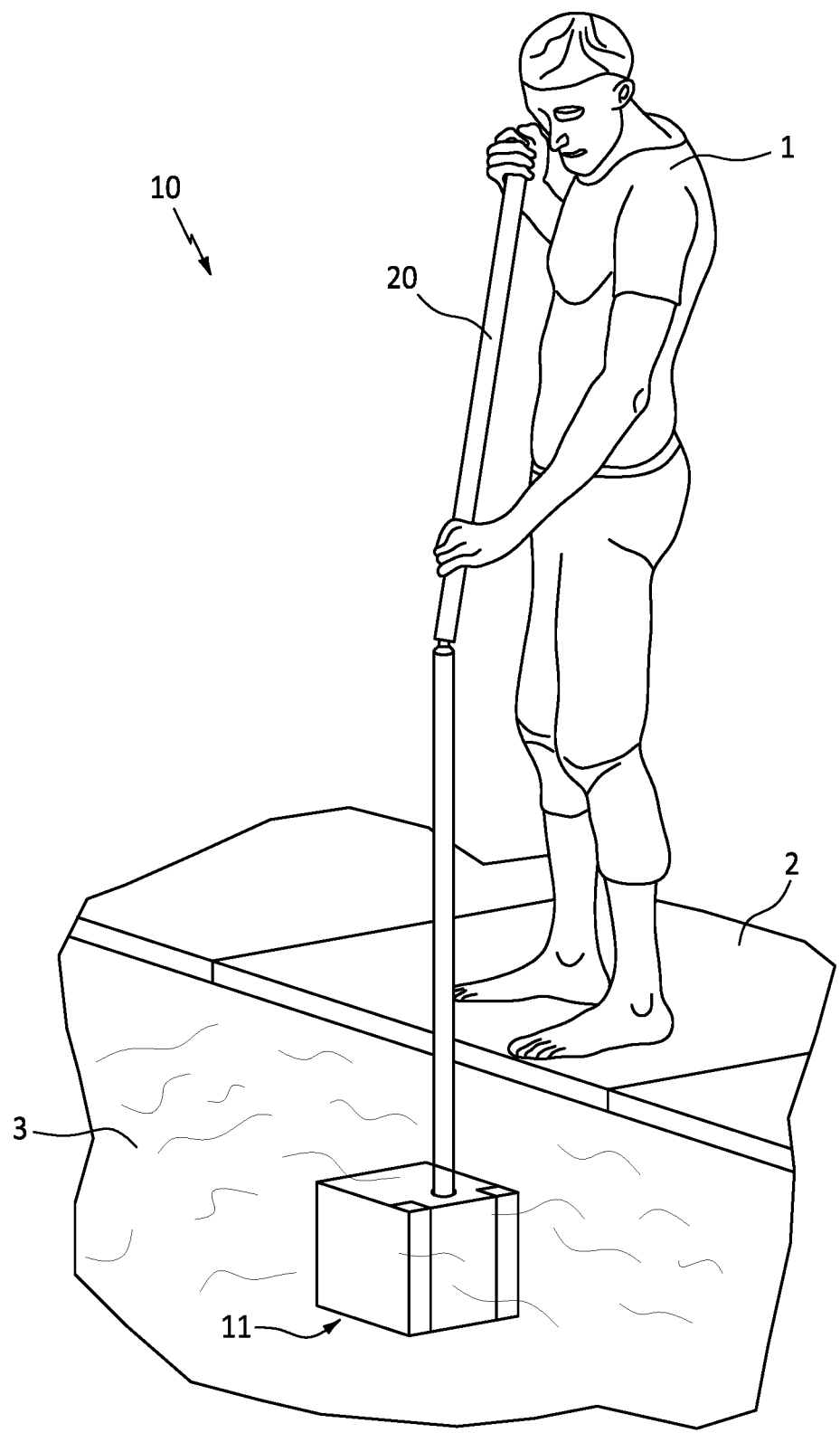
FIG. 6 is a perspective view of the extendable pool water collection and testing device in operation, in accordance with one embodiment of the invention.

FIG. 6 illustrates one embodiment of the device 10 in operation. As shown, a user 1 standing on a deck 2 or other surface can extend the handle 20 and then dip the main body 11 into a body of water 3 without having to kneel or bend. Upon the water entering the chambers, the user can perform chemical or strip testing on the water as described above and can also transport or pour water from the basin into any number of secondary containers for more detailed offsite analysis. Moreover, during this time, items within the pocket will remain dry even as the main body is submerged in water.

Accordingly, the above noted device provides a novel approach for collecting and testing pool water that is not rendered obvious by any known art.

As to a further description of the manner and use of the present invention, the same should be apparent from the above description. Accordingly, no further discussion relating to the manner of usage and operation will be provided.

As described herein, one or more elements of the device 10 can be secured together utilizing any number of known attachment means such as, for example, screws, glue, compression fittings and welds, among others. Moreover, although the above embodiments have been described as including separate individual elements, the inventive concepts disclosed herein are not so limiting. To this end, one of skill in the art will recognize that one or more individually identified elements may be formed together as one or more continuous elements, either through manufacturing processes, such as welding, casting, or molding, or through the use of a singular piece of material milled or machined with the aforementioned components forming identifiable sections thereof.

The terminology used herein is for the purpose of describing particular embodiments only and is not intended to be limiting of the invention. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Likewise, the term "consisting" shall be used to describe only those components identified. In each instance where a device comprises certain elements, it will inherently consist of each of those identified elements as well.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A device, comprising: a main body having a front wall, a back wall, a top end, a bottom end, and a pair of side walls; a sample collection basin that is positioned adjacent to the back wall and extends between the pair of side walls, said collection basin including an interior space and a basin opening for accessing the interior space; a spout that extends outward from the back wall; a pair of test chambers that are positioned along the front wall of the main body, each of the pair of chambers including a hollow interior space and an opening for accessing the hollow interior space; and a handle that is connected to the main body, wherein each of the test chamber openings, the basin opening, and a top surface of the spout are positioned coplanar with the top end of the main body; a watertight pocket that is positioned along an outside surface of the main body, said watertight pocket being configured to receive and store a plurality of chemical test strips.

2. The device of claim 1, wherein a length of the handle is adjustable.

3. The device of claim 1, wherein an orientation of the handle relative to the orientation of the main body is adjustable.

4. The device of claim 3, further comprising:
an articulating joint that interposed between the handle and the main body.

5. The device of claim 1, wherein the handle is permanently affixed to the main body.

6. The device of claim 1, wherein the handle is removably connected to the main body.

7. The device of claim 1, further comprising:
a plurality of threaded elements located along a bottom end of the handle, and a second plurality of threaded elements located within an aperture on the top end of the main body,
wherein the first plurality of threaded elements and the second plurality of threaded elements function to removably secure the handle onto the top end of the main body.

8. The device of claim 1, wherein the front wall of the main body is transparent.

9. The device of claim 8, wherein the front wall forms a front wall of each of the pair of test chambers.

10. The device of claim 9, further comprising:
a plurality of colored markings that are positioned along the front wall of each of the pair of test chambers, said plurality of colored markings being configured to correspond to a color of a reagent reaction within the pair of test chambers.

11. The device of claim 1, further comprising:
a lid that that is configured to be removably secured onto the top end of the main body and to cover each of the openings on the pair of test chambers and the basin opening.

12. The device of claim 1, further comprising:
a lid that that is configured to be removably secured onto the top end of the main body and to cover each of the openings on the pair of test chambers and the basin opening, and the spout.

13. The device of claim 1, wherein the collection basin is configured to receive and store a greater amount of the liquid from the body of water than each of the pair of chambers.

14. The device of claim 13, wherein the collection basin is configured to receive and store six ounces of the liquid from the body of water.

15. The device of claim 12, wherein the lid includes an opening that is configured to receive the handle when the lid is secured onto the top of the main body.

16. The device of claim 1, further comprising:
another pair of test chambers that are positioned along the back wall of the main body at a location adjacent to the spout, each of the another pair of chambers including a hollow interior space and an opening for accessing the hollow interior space,
wherein the pair of test chambers positioned along the front wall of the main body include a plurality of colored markings that are configured to correspond to a color of a reagent reaction within the pair of test chambers, and
wherein the another pair of test chambers positioned along the back wall of the main body include an unmarked transparent surface for viewing a chemical test strip positioned within the hollow interior space.

* * * * *